United States Patent [19]

Fujii et al.

[11] Patent Number: 4,650,801
[45] Date of Patent: Mar. 17, 1987

[54] ANTI-CANCER COMPOSITIONS FOR DELIVERING 5-FLUOROURACIL

[75] Inventors: Setsuro Fujii, Toyonaka; Norio Unemi; Setsuo Takeda, both of Tokushima, all of Japan

[73] Assignee: Taiho Pharmaceutical Company, Ltd., Tokyo, Japan

[21] Appl. No.: 552,263

[22] Filed: Nov. 16, 1983

Related U.S. Application Data

[63] Continuation of Ser. No. 214,021, Dec. 8, 1980, abandoned, which is a continuation-in-part of Ser. No. 21,317, Mar. 16, 1979, abandoned.

[30] Foreign Application Priority Data

Mar. 27, 1978 [JP] Japan .................................. 53-35834
Jul. 28, 1978 [JP] Japan .................................. 53-92813
Nov. 7, 1978 [JP] Japan .................................. 53-137686

[51] Int. Cl.$^4$ .................................................. A61K 31/505
[52] U.S. Cl. .................................................. 514/274
[58] Field of Search .......................... 424/251; 514/274

[56] References Cited

U.S. PATENT DOCUMENTS 4,328,229 5/1982 Fujii et al. .......................... 424/251
4,481,203 11/1984 Fujii et al. .......................... 424/251
4,507,301 3/1985 Fujii et al. .......................... 424/251

Primary Examiner—Jerome D. Goldberg
Attorney, Agent, or Firm—Murray and Whisenhunt

[57] ABSTRACT

An anti-cancer composition for delivering 5-fluorouracil to cancer tissues which comprises at least one 5-fluorouracil derivative, and a uracil derivative.

12 Claims, No Drawings

ANTI-CANCER COMPOSITIONS FOR DELIVERING 5-FLUOROURACIL

This is a continuation application of Ser. No. 214,021, filed Dec. 8, 1980, now abandoned, which application is in turn a continuation-in-part application of Ser. No. 21,317 filed Mar. 16, 1979, now abandoned.

This invention relates to anti-cancer compositions for delivering 5-fluorouracil.

Extensive research on the chemotherapy of cancers has heretofore been conducted, with the chemotherapy of cancers commenced in the latter half of the 1940's for the control of nucleic acid metabolism. As antimetabolites to nucleic acids, 6-mercaptopurine was synthesized first, followed by the discovery of 5-fluorouracil.

5-Fluorouracil was synthesized by Duschinsky in 1957 and found to have anticancer activity by Heidelberger et al. The compound has a wide anti-cancer spectrum range, produces outstanding effects especially on adenocarcinomas and is therefore one of the anti-cancer agents which are most widely used for clinical purposes. Since 5-fluorouracil is typical of antagonists to nucleic acid metabolism, intensive research is still continued on compounds having 5-fluorouracil as the basic skeleton. Recently reports have been made on several excellent compounds including, for example, 1-(2-tetrahydrofuryl)-5-fluorouracil developed in the Soviet Union as a masked-type compound of 5-fluorouracil. This compound is slowly converted to 5-fluorouracil in vivo almost without producing the direct toxic effect that would result from the administration of 5-fluorouracil. Thus the method has been established in Japan of using the compound for therapy as an oral anti-cancer agent. The compound nevertheless is said to be somewhat inferior to 5-fluorouracil in efficacy, so that it is desired to develop 5-fluorouracil derivatives having still higher anti-cancer activity and reduced side effects which are therapeutically justifiable.

1-(2-Tetrahydrofuryl)-5-fluorouracil is of significant value because it is usable with little or no direct side effect as mentioned above; for example, it can be orally given with a reduced influence on the digestive system. However, the compound still remains to be improved in its anti-cancer effects. While it is generally believed that the derivatives having 5-fluorouracil as the basic skeleton thereof exhibit an anti-cancer effect when converted to 5-fluorouracil in vivo, the insufficient effect observed appears attributable partly to the fact that the resulting 5-fluorouracil is further decomposed and become inactive. For reference, it is said that when 5-fluorouracil is intravenously given, the concentration of the compound in the blood reduces to one-half the initial value in about 15 to about 20 minutes. Shimoyama et al. have suggested that the effects of antimetabolites such as 5-fluorouracil are time-dependent, stating that it is desirable to maintain the antimetabolite at a specified concentration in cancer tissues for a prolonged period of time. It therefore follows that in order to enable 5-fluorouracil derivatives to achieve an improved anti-cancer effect, there is the necessity of impeding the decomposition and inactivation of 5-fluorouracil converted from the derivative in the living body. The result will be more preferable if this can be realized more peculiarly in cancer tissues than in normal tissues. From this viewpoint, we carried out intensive research and found that the foregoing problem could be overcome by the use of a 5-fluorouracil conjointly with uracil. We have already filed patent applications in many countries based on this finding.

We have further conducted continued research in an attempt to obtain anti-cancer compositions for delivering 5-fluorouracils so as to exhibit an enhanced anti-cancer effect and found that the contemplated object can be fulfilled also by the use of a 5-fluorouracil conjointly with a specific compound.

An object of this invention is to provide an anti-cancer composition which contains a 5-fluorouracil and which delivers 5-fluorouracil to the cancer tissue and which enables the 5-fluorouracil to produce an outstanding anti-cancer effect by inhibiting the decomposition and inactivation of 5-fluorouracil converted from the 5-fluorouracil component in vivo.

Another object of this invention is to provide an anti-cancer composition containing a 5-fluorouracil which delivers 5-fluorouracil to cancer tissue and which, therefore, produces a high anti-cancer effect, suppressed toxicity and reduced side effects.

The present invention provides anti-cancer compositions for delivering 5-fluorouracil to cancer tissues in warm-blooded animals, the compositions comprising a pharmaceutically effective amount of at least one 5-fluorouracil (a) and an effective amount of a uracil derivative (b). The uracil derivative (b) is cytosine.

Although the uracil derivative useful in this invention has little or no anti-cancer effect in itself, the conjoint use of the derivative for delivery the 5-fluorouracil produces a greatly enhanced anti-cancer effect and achieves a remarkably improved therapeutic result.

The 5-fluorouracils useful in the invention are 1-(2-Tetrahydrofuryl)-5-fluorouracil (Compound 5) and 3-(2-Tetrahydrofuryl)-5-fluorouracil (Compound 6).

5-Fluorouracil derivatives other than those noted above will similarly be converted to 5-fluorouracil in vivo, presumably giving an increased anti-cancer effect when used conjointly with the above-specified uracil derivative (b).

The compounds noted above are already known. For example, Compound 5 is disclosed in Japanese Published Examined Patent Application No. 10510/1974, and Compound 6 in Japanese Published Unexamined Patent Application No. 51373/1977. Compounds other than those exemplified above, if readily convertible to uracil in vivo, will afford an improved anti-cancer effect when used conjointly for delivering the 5-fluorouracil mentioned above. Especially preferable among useful uracil derivatives of this invention is cytosine. The examples of uracil derivatives given above, except for 1-n-hexylcarbamoyluracil and 1-cyclohexylcarbamoyluracil, are known and can be prepared by known methods, while 1-n-hexylcarbamoyluracil and 1-cyclohexylcarbamoyluracil, which are novel compounds.

The proportions of the 5-fluorouracil and the uracil derivative to be used for preparing the anti-cancer compositions of this invention are not specifically limited but variable depending on the kinds of these compounds. Generally it is preferable to use about 0.5 to 20 moles of the latter per mole of the former.

The anti-cancer compositions of this invention comprising a 5-fluorouracil and a uracil derivative for delivering the 5-fluorouracil to cancers in warm-blooded animals. When the 5-fluorouracil component is converted to 5-fluorouracil in vivo, the presence of the uracil derivative suppresses the decomposition and inactivation of the resulting 5-fluorouracil, consequently permitting the composition to produce an outstanding anti-cancer effect.

According to this invention, the 5-fluorouracil (a) and uracil derivative (b) can be administered to warm-blooded animals individually in separate doses but are given preferably at the same time in the form of a single preparation. The anti-cancer compositions of this invention can be administered in the desired form of preparation in accordance with the therapy contemplated. They are provided for example as tablets, capsules and granules for oral administration or as parenteral solutions and suppositories for non-oral administration. These preparations can be formulated with use of carriers already known in the art.

Examples of useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. The amount of the 5-fluorouracil (a) in the oral preparations may preferably be 10 to 200 mg per dosage unit. Carriers suitable for parenteral preparations are, for example, water, physiological saline solution, etc., which can be used with tris(hydroxymethyl)-aminomethane, sodium carbonate, sodium hydroxide or the like serving as a solubilizer or pH adjusting agent. The parenteral preparations contain preferably 50 to 1,000 mg of the 5-fluorouracil (a) per dosage unit. Suitable carriers for preparing suppositories are, for example, cacao butter, Witepsol-W35 (fat, trade mark of Dynamit Nobel A.G. of Germany). The suppositories may contain preferably 250 to 1,000 mg of the 5-fluorouracil (a) per piece. The daily dose of the present compositions is not specifically limited but can be varied with the kind of the 5-fluorouracil as well as of the uracil derivative. The results of clinical applications and potency tests appear to indicate that preferred doses are usually about 20 to about 1,200 mg for oral preparations, about 50 to about 2,000 mg for parenteral solutions and about 250 to about 2,000 mg for suppositories, all calculated as 5-fluorouracils.

PREPARATION 1

| Preparation 1 | |
| --- | --- |
| Compound 6 | 500 mg |
| Cytosine | 555 mg |
| Witepsol W-35 | 945 mg |
| | 2000 mg (per piece) |

Suppositories are prepared from the above ingredients.

The anti-cancer compositions of this invention are tested in mice by the following methods to determine acute toxicity, anti-cancer effect and therapeutic index (a) Acute toxicity Male mice of ICR strain weighing 22±1 g are used, 5 mice in each group. A 5-fluorouracil (a) and uracil derivative (b) in the proportions listed in Tables 1-16 are suspended in a 5% solution of gum arabic to prepare a suspension, which is forcibly orally administered to each mouse through a tube at a dose of 1 ml/100 g. Over the following period of three weeks the mice are checked every day for poisoning, body weight and mortality. The $LD_{50}$ is determined according to the up-and-down method 3 weeks after the administration. The results are given in Tables 1-16.

(b) Anti-cancer effect

Tissues of sarcoma 180, $2 \times 10^6$, are subcutaneously transplanted in the back of male mice of ICR strain (6 mice in each group). A 5-fluorouracil (a) and uracil derivative (b) in the proportions listed in Tables 1-16 are suspended in a 5% solution of gum arabic to prepare a suspension. Twenty-four hours after the transplantation and during the following seven consecutive days the suspension is orally given to the animal once every day. On the 10th day after the transplantation, the tumor is removed from the body and weighed to calculate the average weight (T) of the tumors in the group to which the composition has been given and the corresponding weight (C) in the control group to determine the ratio T/C. The effective dose ($ED_{50}$) for achieving 50% cancer inhibition is determined from the dose-response curve involving the dose and effect (T/C). The results are given in Tables 1-16.

(c) Therapeutic index

The $LD_{50}$ and $ED_{50}$ values obtained above are used to determine the therapeutic index ($LD_{50}/ED_{50}$). The results are also listed in Tables 1-16.

TABLE 1

| 5-Fluorouracil (a) (Compd. No.) | (b)/(a) mol ratio | $LD_{50}$ (mg/kg) | $ED_{50}$ (mg/kg) | Therapeutic Index ($LD_{50}/ED_{50}$) |
| --- | --- | --- | --- | --- |
| 5 | 0 | 820 | 140 | 5.9 |
|  | 0.5 | 794 | 129 | 6.2 |
|  | 2 | 635 | 55 | 11.5 |
|  | 10 | 529 | 36 | 14.7 |
| 6 | 0 | 1021 | 73 | 13.1 |
|  | 1 | 945 | 43 | 22.0 |
|  | 2 | 815 | 31 | 26.3 |
|  | 20 | 597 | 29 | 20.6 |

(b) = Uridine

TABLE 2

| 5-Fluorouracil (a) (Compd. No.) | (b)/(a) mol ratio | $LD_{50}$ (mg/kg) | $ED_{50}$ (mg/kg) | Therapeutic Index ($LD_{50}/ED_{50}$) |
| --- | --- | --- | --- | --- |
| 5 | 0 | 820 | 140 | 5.9 |
|  | 0.5 | 808 | 82 | 9.9 |
|  | 2 | 635 | 37 | 17.2 |
|  | 10 | 471 | 28 | 16.8 |
| 6 | 0 | 1021 | 73 | 13.1 |
|  | 1 | 845 | 53 | 15.9 |
|  | 2 | 790 | 42 | 18.8 |
|  | 20 | 525 | 26 | 20.2 |

(b) = 2'-Deoxyuridine

TABLE 3

| 5-Fluorouracil (a) (Compd. No.) | (b)/(a) mol ratio | $LD_{50}$ (mg/kg) | $ED_{50}$ (mg/kg) | Therapeutic Index ($LD_{50}/ED_{50}$) |
| --- | --- | --- | --- | --- |
| 5 | 0 | 820 | 140 | 5.9 |
|  | 1 | 340 | 42 | 8.1 |
|  | 2 | 283 | 28 | 10.1 |
|  | 10 | 189 | 14 | 13.5 |
| 6 | 0 | 1021 | 73 | 13.1 |
|  | 0.5 | 830 | 48 | −17.3 |
|  | 2 | 537 | 27 | 19.9 |
|  | 10 | 324 | 14 | 23.1 |

(b) = Thymine

TABLE 4

| 5-Fluorouracil (a) (Compd. No.) | (b)/(a) mol ratio | $LD_{50}$ (mg/kg) | $ED_{50}$ (mg/kg) | Therapeutic Index ($LD_{50}/ED_{50}$) |
|---|---|---|---|---|
| 5 | 0 | 820 | 140 | 5.9 |
|   | 1 | 800 | 112 | 7.1 |
|   | 2 | 800 | 72 | 11.1 |
|   | 20 | 667 | 59 | 11.3 |
| 6 | 0 | 1021 | 73 | 13.1 |
|   | 1 | 1020 | 69 | 14.8 |
|   | 2 | 969 | 61 | 15.9 |
|   | 20 | 806 | 46 | 17.5 |

(b) = Orotic acid

TABLE 5

| 5-Fluorouracil (a) (Compd. No.) | (b)/(a) mol ratio | $LD_{50}$ (mg/kg) | $ED_{50}$ (mg/kg) | Therapeutic Index ($LD_{50}/ED_{50}$) |
|---|---|---|---|---|
| 5 | 0 | 820 | 140 | 5.9 |
|   | 1 | 570 | 55 | 10.4 |
|   | 2 | 380 | 26 | 14.6 |
|   | 10 | 253 | 23 | 11.0 |
| 6 | 0 | 1021 | 73 | 13.1 |
|   | 0.5 | 745 | 39 | 19.1 |
|   | 2 | 575 | 26 | 22.1 |
|   | 10 | 412 | 21 | 19.6 |

(b) = 5-Bromouracil

TABLE 6

| 5-Fluorouracil (a) (Compd. No.) | (b)/(a) mol ratio | $LD_{50}$ (mg/kg) | $ED_{50}$ (mg/kg) | Therapeutic Index ($LD_{50}/ED_{50}$) |
|---|---|---|---|---|
| 5 | 0 | 820 | 140 | 5.9 |
|   | 1 | 567 | 54 | 10.5 |
|   | 2 | 252 | 24 | 10.5 |
|   | 10 | 168 | 17 | 12.9 |
| 6 | 0 | 1021 | 73 | 13.1 |
|   | 0.5 | 640 | 49 | 13.1 |
|   | 2 | 478 | 30 | 15.9 |
|   | 10 | 308 | 22 | 14.0 |

(b) = 5-Bromo-2'-deoxyuridine

TABLE 7

| 5-Fluorouracil (a) (Compd. No.) | (b)/(a) mol ratio | $LD_{50}$ (mg/kg) | $ED_{50}$ (mg/kg) | Therapeutic Index ($LD_{50}/ED_{50}$) |
|---|---|---|---|---|
| 5 | 0 | 820 | 140 | 5.9 |
|   | 1 | 302 | 32 | 9.4 |
|   | 2 | 168 | 17 | 9.9 |
|   | 5 | 112 | 12 | 9.3 |
| 6 | 0 | 1021 | 73 | 13.1 |
|   | 1 | 467 | 26 | 18.0 |
|   | 2 | 380 | 17 | 22.4 |
|   | 5 | 194 | 11 | 17.6 |

(b) = 5-Iodouracil

TABLE 8

| 5-Fluorouracil (a) (Compd. No.) | (b)/(a) mol ratio | $LD_{50}$ (mg/kg) | $ED_{50}$ (mg/kg) | Therapeutic Index ($LD_{50}/ED_{50}$) |
|---|---|---|---|---|
| 5 | 0 | 820 | 140 | 5.9 |
|   | 1 | 678 | 99 | 6.8 |
|   | 2 | 565 | 38 | 14.9 |
|   | 10 | 377 | 34 | 11.1 |
| 6 | 0 | 1021 | 73 | 13.1 |
|   | 1 | 874 | 51 | 17.1 |
|   | 2 | 650 | 29 | 22.4 |
|   | 5 | 535 | 18 | 29.7 |

(b) = 1-(2-Tetrahydrofuryl)uracil

TABLE 9

| 5-Fluorouracil (a) (Compd. No.) | (b)/(a) mol ratio | $LD_{50}$ (mg/kg) | $ED_{50}$ (mg/kg) | Therapeutic Index ($LD_{50}/ED_{50}$) |
|---|---|---|---|---|
| 5 | 0 | 820 | 140 | 5.9 |
|   | 1 | 499 | 49 | 10.2 |
|   | 2 | 333 | 31 | 10.7 |
|   | 5 | 222 | 16 | 8.9 |
| 6 | 0 | 1021 | 73 | 13.1 |
|   | 1 | 702 | 32 | 21.9 |
|   | 2 | 468 | 26 | 18.0 |
|   | 5 | 246 | 16 | 15.4 |

(b) = 1-Acetyluracil

TABLE 10

| 5-Fluorouracil (a) (Compd. No.) | (b)/(a) mol ratio | $LD_{50}$ (mg/kg) | $ED_{50}$ (mg/kg) | Therapeutic Index ($LD_{50}/ED_{50}$) |
|---|---|---|---|---|
| 5 | 0 | 820 | 140 | 5.9 |
|   | 1 | 746 | 98 | 7.6 |
|   | 2 | 621 | 37 | 16.8 |
|   | 10 | 509 | 30 | 17.0 |
| 6 | 0 | 1021 | 73 | 13.1 |
|   | 1 | 768 | 42 | 18.3 |
|   | 2 | 663 | 32 | 20.7 |
|   | 10 | 448 | 25 | 17.9 |

(b) = 3-Benzoyluracil

TABLE 11

| 5-Fluorouracil (a) (Compd. No.) | (b)/(a) mol ratio | $LD_{50}$ (mg/kg) | $ED_{50}$ (mg/kg) | Therapeutic Index ($LD_{50}/ED_{50}$) |
|---|---|---|---|---|
| 5 | 0 | 820 | 140 | 5.9 |
|   | 0.5 | 771 | 113 | 6.8 |
|   | 2 | 643 | 55 | 11.2 |
|   | 5 | 428 | 36 | 11.9 |
| 6 | 0 | 1021 | 73 | 13.1 |
|   | 0.5 | 833 | 55 | 15.1 |
|   | 2 | 694 | 46 | 15.1 |
|   | 5 | 576 | 33 | 17.5 |

(b) = 1-Cyclohexylcarbamoyluracil

TABLE 12

| 5-Fluorouracil (a) (Compd. No.) | (b)/(a) mol ratio | $LD_{50}$ (mg/kg) | $ED_{50}$ (mg/kg) | Therapeutic Index ($LD_{50}/ED_{50}$) |
|---|---|---|---|---|
| 5 | 0 | 876 | 134 | 6.5 |
|   | 0.5 | 876 | 112 | 7.8 |
|   | 2 | 584 | 52 | 10.3 |
|   | 10 | 443 | 43 | 11.3 |
| 6 | 0 | 1021 | 73 | 13.1 |
|   | 1 | 928 | 59 | 15.7 |
|   | 2 | 844 | 41 | 20.6 |
|   | 10 | 469 | 28 | 16.8 |

(b) = 1-n-Hexylcarbamoyluracil

TABLE 13

| 5-Fluorouracil (a) (Compd. No.) | (b)/(a) mol ratio | $LD_{50}$ (mg/kg) | $ED_{50}$ (mg/kg) | Therapeutic Index ($LD_{50}/ED_{50}$) |
|---|---|---|---|---|
| 5 | 0 | 876 | 134 | 6.5 |
|   | 1 | 876 | 108 | 8.1 |
|   | 2 | 820 | 66 | 12.4 |
|   | 20 | 276 | 27 | 10.2 |
| 6 | 0 | 1021 | 73 | 13.1 |
|   | 1 | 1021 | 56 | 18.2 |
|   | 2 | 1021 | 41 | 24.9 |
|   | 10 | 639 | 24 | 26.6 |

(b) = Cytosine

TABLE 14

| 5-Fluorouracil (a) (Compd. No.) | (b)/(a) mol ratio | LD$_{50}$ (mg/kg) | ED$_{50}$ (mg/kg) | Therapeutic Index (LD$_{50}$/ED$_{50}$) |
|---|---|---|---|---|
| 5 | 0 | 876 | 134 | 6.5 |
|   | 1 | 876 | 98 | 8.9 |
|   | 2 | 796 | 70 | 11.4 |
|   | 20 | 266 | 28 | 9.5 |
| 6 | 0 | 1021 | 73 | 13.1 |
|   | 1 | 1021 | 58 | 17.6 |
|   | 2 | 928 | 39 | 23.8 |
|   | 10 | 773 | 34 | 22.7 |

(b) = Cytidine

TABLE 15

| 5-Fluorouracil (a) (Compd. No.) | (b)/(a) mol ratio | LD$_{50}$ (mg/kg) | ED$_{50}$ (mg/kg) | Therapeutic Index (LD$_{50}$/ED$_{50}$) |
|---|---|---|---|---|
| 5 | 0 | 876 | 134 | 6.5 |
|   | 1 | 876 | 102 | 8.6 |
|   | 2 | 796 | 69 | 11.5 |
|   | 20 | 334 | 39 | 8.6 |
| 6 | 0 | 1021 | 73 | 13.1 |
|   | 1 | 928 | 59 | 15.7 |
|   | 2 | 843 | 47 | 17.9 |
|   | 10 | 680 | 34 | 20.0 |

(b) = 2'-Deoxycytidine

TABLE 16

| 5-Fluorouracil (a) (Compd. No.) | (b)/(a) mol ratio | LD$_{50}$ (mg/kg) | ED$_{50}$ (mg/kg) | Therapeutic Index (LD$_{50}$/ED$_{50}$) |
|---|---|---|---|---|
| 5 | 0 | 820 | 140 | 5.9 |
|   | 2 | 636 | 94 | 6.8 |
|   | 5 | 424 | 42 | 10.1 |
|   | 10 | 339 | 40 | 8.5 |
| 6 | 0 | 1021 | 73 | 13.1 |
|   | 0.5 | 963 | 67 | 14.4 |
|   | 2 | 886 | 63 | 14.1 |
|   | 10 | 639 | 60 | 10.7 |

(b) = Thymidine

Variations of the concentration of 5-fluorouracil in the cancer cellular tissue with the lapse of time are determined by the following method when the 5-fluorouracil derivative (a) is administered to rats having cancer:

$^3$H-FT-207 (300 μ Ci/Kg) with cytosine were suspended in 5% acasia solution and administered orally to AH 130 bearing rats through a stomach tube, each of 3 rats/group. FT-207 is 1-(2-tetrahydrofuryl)-5-fluorouracil. The rat were sacrified at various periods, the tumors were removed and used for analysis. Tumor were homogenized in a equal volume of saline, 1.0 ml of each sample was suspended in 7 volumes of cold methanol and centrifuged at 3000 rpm for 10 min. The precipitate was washed twice with 2 volumes of cold methanol and the mixture was centrifuged. The supernatant was combined with first supernatant and dried under nitrogen. The dried material was dissolved in 100 μl of 50% methanol and an aliquot (10 μl) was applied to thin layer chromatography (TLC) plate (TLC plate: Kieselgel 60 F254 pre-coated, 2×20 cm, thickness 0.25 mm, Merck) beforehand carrier FT-207 and 5-fluorouracil (5-FU) were applied, and developed in a solvent composed of chloroform: ethylacetate (1:9 V/V). After development, the spot of 5-FU(Rf 0.20) was separated from FT-207 (Rf 0.47), and 5-FU fraction was scraped off, placed in a vial and extracted with 0.2 ml of methanol for 2 hr. Samples were mixed with 10 ml of scintillator containing 4 g of 2,5-diphenyloxazole, 0.4 g of 1,4-bis-[2-(4-methyl-5-phenyloxazolyl)]benzene and 100 g of naphthalene per liter of solvent composed of dioxane: toluene: ethylcellosolve=15:3:2 (v/v/v), and the radio activity was measured with Aloka LSC 673 liquid scintillation spectrometer. Test results will each alone administration of FT-207 cytosine are also shown in Table below.

TABLE 17

| Component and dosage (m · mol/Kg) | | mole ratio | Concentration of 5-FU (μg/ml) in cancer tissues | | | |
|---|---|---|---|---|---|---|
| | | | 1 hr | 2 hr | 4 hr | 8 hr |
| FT-207 0.075 | Cytosine 0.0375 | 1:0.5 | 0.067 | 0.068 | 0.053 | 0.040 |
|  | 0.75 | 1:10 | 0.087 | 0.089 | 0.129 | 0.123 |
|  | 1.5 | 1:20 | 0.113 | 0.112 | 0.180 | 0.144 |
| FT-207 0.075 alone | | — | 0.049 | 0.044 | 0.021 | 0.019 |
| FD-1 0.0185 alone | | — | 0.033 | 0.024 | 0.011 | 0.008 |
| Cytosine 1.5 alone | | — | 0.000 | 0.000 | 0.000 | 0.000 |
| Cytidine 1.5 alone | | — | 0.000 | 0.000 | 0.000 | 0.000 |
| 2'-Deoxycytidine 1.5 alone | | — | 0.000 | 0.000 | 0.000 | 0.000 |

As will be appreciated from the 5-fluorouracil concentration values reported hereinabove, the anti-cancer composition of the present invention functions in the manner of a prodrug. That is, the 5-fluorouracil derivative (a) such as 1-(2-tetrahydrofuryl)-5-fluorouracil in the anti-cancer composition of the present invention is converted in the body into 5-fluorouracil. The concentration of 5-fluorouracil maintained in the cancer cellular tissue of test animals for a prolonged period of time is much higher when the 5-fluorouracil derivative (a) is administered with uracil derivative (b) such as cytosine, than when the 5-fluorouracil derivative (a) is administered alone. The composition of the present invention thus functions as a delivery system for delivering 5-fluorouracil to a cancer. The cancers which respond to the present treatment are those cancers which are sensitive to 5-fluorouracil therapy. Thus, as will be clear from the values reported in Table 17 hereinabove, cancers sensitive to 5-fluorouracil therapy are treated by administering to a warm blooded animal having such cancer an effective amount of the 5-fluorouracil derivative, together with uracil derivative and a pharmaceutical excipient. The excipient is, preferably, sterile.

As known to those in the art, the cancers which are sensitive to 5-fluorouracil therapy include breast cancer, cancer of the esophagus, lung cancer, liver cancer and cancers of the gastro-intestinal system, such as stomach cancer, cancers of the intestines, cancer of the rectum, and the like.

We claim:
1. An anti-cancer composition for delivering 5-fluorouracil to cancer tissues sensitive to 5-fluorouracil, in warm-blooded animals, said composition comprising an effective amount to deliver at least one 5-fluorouracil selected from the group consisting of 1-(2-tetrahy- drofuryl)-5-fluorouracil and 3-(2-tetrahydrofuryl)-5-fluorouracil and an effective amount of cytosine, wherein about 0.5 to about 20 mols of cytosine is used per mole of the 5-flurouracil.

2. An anti-cancer composition as defined in claim 1 wherein about 1 to 20 mols of the cytosine is used per mole of the 5-fluorouracil.

3. An anti-cancer composition as defined in claim 2 wherein about 2 to about 10 mols of the cytosine is used per mole of the 5-fluorouracil.

4. An anti-cancer composition as defined in claim 1 which is an oral preparation.

5. An anti-cancer composition as defined in claim 1 which is a parenteral solution.

6. An anti-cancer composition as defined in claim 1 which is a suppository.

7. An anti-cancer composition as defined in claim 1 wherein the 5-fluorouracil is 1-(2-tetrahydrofuryl)-5-fluorouracil.

8. An anti-cancer composition as defined in claim 1 wherein the 5-fluorouracil is 3-(2-tetrahydrofuryl)-5-fluorouracil.

9. A method of delivering a 5-fluorouracil to a cancer sensitive to a 5-fluorouracil in a warm-blooded animal, the method comprising administering to the animal an effective amount to deliver 5-fluorouracil of the composition of claim 1 in the form of a single preparation.

10. A method of delivering a 5-fluorouracil to a cancer sensitive to a 5-fluorouracil in a warm-blooded animal, the method comprising administering to the animal, an effective amount to deliver at least one 5-fluorouracil selected from the group consisting of 1-(2-tetrahydrofuryl)-5-fluorouracil and 3-(2-tetrahydrofuryl)-5-fluorouracil and cytosine in separate doses, and wherein about 0.5 to about 20 mols of cytosine is used per mole of the 5-fluorouracil.

11. The method of claim 10 wherein the 5-fluorouracil is 1-(2-tetrahydrofuryl)-5-fluorouracil.

12. The method of claim 10 wherein the 5-fluorouracil is 3-(2-tetrahydrofuryl)-5-fluorouracil.

* * * * *